Dec. 1, 1964 C. L. ROBERTS Plant Pat. 2,460
APPLE TREE
Filed Sept. 19, 1963
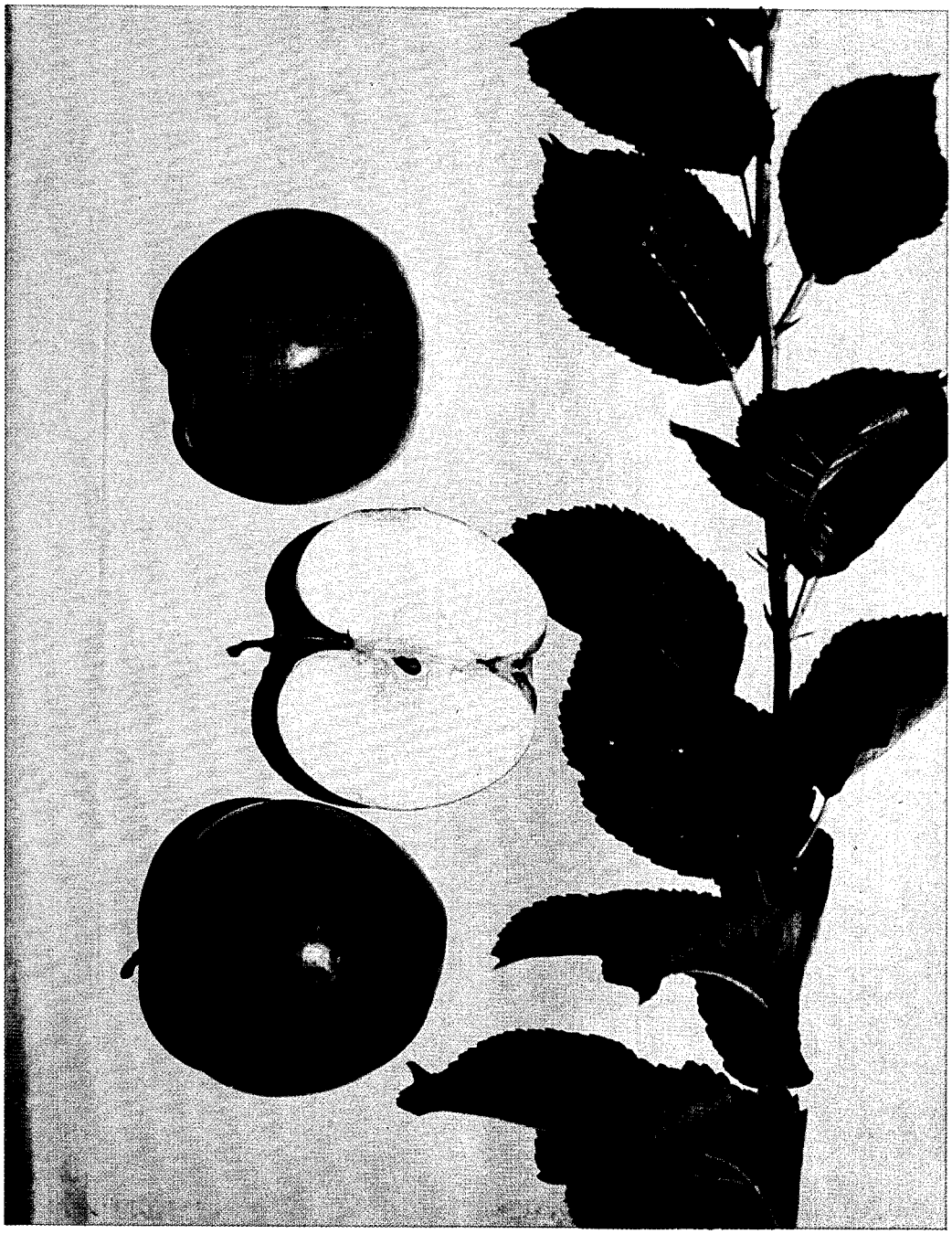
Inventor.
Charles L. Roberts
By: Robb & Robb
Attorneys.

United States Patent Office

Plant Pat. 2,460
Patented Dec. 1, 1964

2,460
APPLE TREE

Charles L. Roberts, Napier, New Zealand, assignor to Stark Bro's Nurseries & Orchards Company, Louisiana, Mo., a corporation of Missouri Filed Sept. 19, 1963, Ser. No. 310,180
1 Claim. (Cl. Plt.—34)

The present invention relates to a new and distinct variety of apple tree which was discovered by me as a newly found seedling of unknown parentage on my cultivated orchard property at Napier, New Zealand.

At the time of my discovery aforesaid, my attention was attracted to the new seedling by reason of the fact that it bore fruit which was generally similar to the fruit of the variety known as the Mullins apple (unpatented and distributed in the United States under the name "Golden Delicious") in respect to the shape, size, texture and flavor of the fruit, but which was bright red in color, contrary to the normal yellow color of the fruit of the Mullins variety. Further study and testing of the fruit of the new seedling disclosed that it had longer keeping qualities and no tendency to shrivel in storage, contrary to the fruit of the Mullins variety.

Asexual reproduction of my new variety, as performed by grafting in New Zealand, confirmed that the foregoing characteristics come true and are established and transmitted through succeeding propagations. Despite the uncertainty of the parentage of my new seedling, I am convinced that it represents a new and distinct variety, and is differentiated from all other varieties by the unique combination of characteristics referred to in the foregoing.

The accompanying drawing shows typical specimens of the fruit and foliage of the new variety as depicted in color as nearly true as it is reasonably possible to make the same in a color illustration of this character, with certain of the fruit specimens being shown in elevation, and one of the fruit specimens being shown in cross-section.

The following is a detailed description of my new variety, with terminology in accordance with the Munsell Color Chart, published by Munsell Color Company, Inc., of Baltimore, Maryland (hereinafter abbreviated as "Munsell") and the Horticultural Colour Guide (hereinafter abbreviated as "HCG"), as indicated, except where general color terms of ordinary dictionary significance are obvious:

Locality where grown and observed: Fruit Research Orchard, Havelock North, New Zealand.

Dates of first and last pickings: March 21 and April 21 (commercial) or June 10 (garden), respectively.

Tree: Medium small size; medium vigorous; spreading; low; round-topped; rapid growing; hardy; very productive; regular bearer.

*Trunk.*—Medium stockiness; shaggy; with burr-knots.

*Branches.* — Medium thickness; shaggy, much-branched; with many spurs. Color—Brown, with varnished twigs of Reddish Brown, Plate 2.5R 2/4 (Munsell).

*Lenticels.*—Numerous; medium large.

*Leaves.*—Large; medium width; medium length; oval; taper-pointed; medium thin; rugose. Length—about 3½ inches. Width—about 2½ inches. Color—Dark Green, Plate 5GY 3/3 (Munsell). Margin—coarsely serrate. Petiole—long, about 1 inch; thick.

Flowers: Medium late in comparison with other varieties; medium large size.

*Dates of first and full bloom.*—October 10 and October 26, respectively (similar to the Mullins apple variety in New Zealand).

*Color.*—Mostly white petals with portions of petals and veins being Light Purplish Pink, Plate 5RP 5/10 (Munsell).

Fruit:

*Maturity when described.*—Eating ripe (April 14).

*Size.*—Uniform. Axial diameter—about 2½ inches. Transverse diameter—about 3 inches.

*Form.*—Ovoid-conical; slightly ribbed.

*Cavity.*—Symmetrical at base; acute; even. Depth—about ⅝ inch. Breadth—1½ inches. Markings—color—fine russet.

*Basin.*—Symmetrical; narrow, furrowed; crowned. Depth—about ⅜ inch. Breadth about 1 inch. Markings—none.

*Stem.*—Clubbed; medium stoutness; slightly pubescent. Length—about 1¼ inches. Breadth—about 1/12 inch.

*Calyx.*—Closed; segments persistent; narrowly lanceolate; acute; about ¼ inch long; approximate at base; ascending; reflexed from base to apex; outer surface slightly pubescent; inner surface pubescent.

*Eye.*—Medium large; partially closed.

*Skin.*—Thin; tender; smooth; glossy; waxed. Dots—conspicuous; few; large; even; circular; color—cream; distribution—evenly scattered. Ground color—Lemon Yellow, Plate 4/2, page 4, vol. 1 (HCG). Color markings—blushed or self-colored; bright; color—Geranium Lake, Plate 20, page 20, vol. 1 (HCG).

*Bloom.*—Wanting.

*Scarfskin.*—Light; confined to stem cavity. Color—white.

*General color effect.*—Bright red.

*Flesh.*—Very juicy. Color—satiny yellowish color. Texture—tender; fine; crisp. Flavor—sweet; rich. Aroma—distinct. Quality—best (comparable to the Mullins variety).

*Core.*—Median. Bundle area—small; narrowly ovate; symmetrical and acute at base; opposite and alternate. Halves of core—equal. Bundles—inconspicuous; in one whorl; color—yellowish green. Alternate bundle—approximate to tube below stamens. Core lines—meeting; indistinct in cross-section. Carpellary area—indistinct; small. Calyx tube—glabrous; narrowly cone-shaped; depth of tube to shoulder—about ⅜ inch; entire depth—about ⅝ inch. Styles—present; distinct to base; pubescent toward base. Stamens—in one distinct whorl; median. Axillary cavity—present. Seed cells—axile; closed. Cell walls—approximate; thin; length—about ¾ inch; breadth—about ⅜ inch. Longitudinal section—broadly obovate; acute at apex, surface fissured. Cross section—narrow.

Seeds:

*Number.*—Usually 8 perfect and 1 imperfect, with largest number about 10; usually 2 seeds per cell.

*Length.*—About 3/8 inch.
*Breadth*—About 3/16 inch.
*Form.*—Acute.
*Color.*—Dark brown.

Use: Market; local; dessert.

Keeping quality: Good; keeps about 180 days in ordinary storage.

Insect and disease resistance: Good resistance to both insects and diseases of the usual kinds to which apple varieties are normally subject in New Zealand, as determined by comparison with other varieties grown under the same conditions in New Zealand.

I claim:

A new and distinct variety of apple tree, substantially as herein shown and described, characterized particularly as to novelty by the general similarity of its fruit in shape, size, texture and flavor to the fruit of the Mullins apple variety (unpatented), but being distinguished therefrom by the bright red color of the fruit, long keeping qualities, and absence of any tendency of the fruit to shrivel in storage.

No references cited.